US012625133B2

(12) United States Patent
Lauber et al.

(10) Patent No.: US 12,625,133 B2
(45) Date of Patent: May 12, 2026

(54) CHEMICAL DENATURATION FOR OLIGONUCLEOTIDE ANALYSIS

(71) Applicant: Waters Technologies Corporation, Milford, MA (US)

(72) Inventors: Matthew A Lauber, North Smithfield, RI (US); Jennifer M. Nguyen, Uxbridge, MA (US); Xiaoxiao Liu, Natick, MA (US); Michael Donegan, Charlton, MA (US)

(73) Assignee: Waters Technologies Corporation, Milford, MA (US)

( * ) Notice: Subject to any disclaimer, the term of this patent is extended or adjusted under 35 U.S.C. 154(b) by 792 days.

(21) Appl. No.: 17/976,030

(22) Filed: Oct. 28, 2022

(65) Prior Publication Data

US 2023/0136953 A1 May 4, 2023

Related U.S. Application Data

(60) Provisional application No. 63/273,294, filed on Oct. 29, 2021.

(51) Int. Cl.

*C12Q 1/68* (2018.01)
*C12Q 1/6806* (2018.01)
*G01N 33/53* (2006.01)
*G01N 33/92* (2006.01)

(52) U.S. Cl.

CPC ....... *G01N 33/5308* (2013.01); *C12Q 1/6806* (2013.01); *G01N 33/92* (2013.01)

(58) Field of Classification Search

CPC ........................................................ C12Q 1/68
See application file for complete search history.

(56) References Cited

U.S. PATENT DOCUMENTS

| | | | | |
|---|---|---|---|---|
| 6,040,440 | A * | 3/2000 | Graham | C07H 17/08 536/7.2 |
| 2005/0222064 | A1* | 10/2005 | Vargeese | A61K 47/60 514/400 |
| 2014/0326268 | A1 | 11/2014 | Philippe et al. | |
| 2017/0081274 | A1* | 3/2017 | Kudryavtsev | C07C 211/64 |
| 2021/0388022 | A1* | 12/2021 | Liu | C07D 487/04 |
| 2022/0017887 | A1 | 1/2022 | Donegan et al. | |

FOREIGN PATENT DOCUMENTS

| | | | | |
|---|---|---|---|---|
| CN | 104419746 | A | 3/2015 | |
| EP | 1870135 | A2 * | 12/2007 | A61Q 5/08 |
| WO | 2021250480 | A1 | 12/2021 | |
| WO | 2022015801 | A1 | 1/2022 | |
| WO | 20220158001 | A1 | 7/2022 | |

OTHER PUBLICATIONS

Hou et al. "Lipid nanoparticles for mRNA delivery." Nat. Rev. Mater. (2021).

International Search Report and Written Opinion issued in International Patent Application No. PCT/IB2022/060393 dated Feb. 1, 2023.

Meingast et al. "Physiochemical properties of enveloped viruses and arginine dictate inactivation." Biotech. J. 16.7 (2021): 2000342.

Sips et al. "LC-MS quantification of oligonucleotides in biological matrices with SPE or hybridization extraction." Bioanal. 11.21(2019): 1941-1954.

Southan et al. "Amidines are potent inhibitors of nitric oxide synthases: preferential inhibition of the inducible isoform." Eur. J. Pharmacol. 291(1995): 311-318.

* cited by examiner

*Primary Examiner* — Kenneth R Horlick
(74) *Attorney, Agent, or Firm* — WOMBLE BOND DICKINSON (US) LLP; Deborah M. Vernon; Ricardo Joseph

(57) ABSTRACT

The present disclosure provides compositions and methods for sample processing, particularly for oligonucleotide analysis e.g. analysis of formulated nucleic acid drugs. A composition for pretreating at least one target nucleic acid in a biological mixture provided herein includes a chaotropic agent selected from a substituted guanidine, a substituted amidine, a substituted quaternary amine, or a combination thereof, an optional protease, and/or an optional disulfide-reducing agent. Methods of analyzing at least one target nucleic acid in a biological mixture is also provided herein. Furthermore, the present disclosure provides methods for quantifying at least one target cationic lipid interacting with a nucleic acid.

18 Claims, 3 Drawing Sheets

CHEMICAL DENATURATION FOR OLIGONUCLEOTIDE ANALYSIS

CROSS-REFERENCE TO RELATED APPLICATION

This application claims priority and benefit to U.S. Provisional Patent Application No. 63/273,294, filed on Oct. 29, 2021, and entitled "CHEMICAL DENATURATION FOR OLIGONUCLEOTIDE ANALYSIS", the contents of which is incorporated herein by reference in its entirety.

FIELD OF THE TECHNOLOGY

The present disclosure generally relates to composition and methods for sample pretreatment prior to qualitative and/or quantitative detection of oligonucleotides. Specifically, this disclosure relates to pretreating at least one target nucleic acid in a biological mixture prior to bioanalytical analysis. The compositions of the present disclosure include a chaotropic agent, an optional protease, and/or an optional disulfide-reducing agent. The present disclosure also relates to methods for detecting at least one target cationic lipid interacting with a nucleic acid.

BACKGROUND

Oligonucleotides are increasingly being developed as direct therapeutic agents against a wide range of disease conditions. They have attracted increasing attention from the biopharmaceutical industry due to the successes of applying this new modality for the treatment of rare diseases as well as their potential in treating common diseases and even viruses, such as SARS-CoV-2 (COVID-19). Therefore, detection and determination of oligonucleotides and their metabolites has become prominent for drug development and evaluation.

However, analyzing oligonucleotides and their metabolites from complex biological matrices such as blood, plasma, tissue, urine presents significant challenges as complex matrices introduce a host of potential interferences such as salts, proteins, lipids, membrane constituents and macromolecular complexes such as ribosomes, spliceosomes, and histones. Any one of these interferences can make it a challenge to obtain accurate and reliable results. Unlike protein-based drugs that generally only bind to extracellular soluble targets or targets on the cell surface, oligonucleotide therapeutics must reach the intracellular targets in the cytoplasm and nucleus to exert pharmacological activities, and as such oligonucleotide therapeutics are by their design made to exhibit a very high degree of protein binding. With this in mind, bioanalytical analysis of oligonucleotides in a biological matrix requires extraction of these highly bound oligonucleotides from freely circulating plasma, from cell surface proteins and also from intercellular domains. The most commonly used techniques to facilitate extraction include protein precipitation (PPT), liquid-liquid extraction (LLE), and solid phase extraction (SPE). These extraction techniques can be used individually or as a combination. However, these traditional techniques suffer from low extraction recoveries, long preparation times, and significant sample manipulation, which can lead to oligo degradation, and limited ability to multiplex the method in an automated format. Critically, as the time for extraction from a biological matrix increases, considerations such as ex vivo conversion of oligonucleotides via nuclease activity could lead to obtaining inaccurate data.

SUMMARY

In general, it is an object of the present technology to obviate or mitigate at least one disadvantage of previous methods for detection and quantification of oligonucleotides in biological matrices.

In general, sample pretreatment methods of the present technology can be utilized to control cell lysis and biological sample disruption for accurate quantification of oligonucleotides and/or lipids using bioanalytical techniques.

In one aspect, provided herein is a method for disrupting the local microenvironment of at least one target nucleic acid in a biological sample in order to accurately quantify and detect the at least one target nucleic acid in the biological sample.

In another aspect, the compositions and methods provided herein are useful for developing sensitive and robust analytical methods for identification, mapping, and relative quantitation of impurities in therapeutic oligonucleotides.

In one aspect, methods provided herein also disrupt the interaction between at least one target cationic lipid and an oligonucleotide, e.g., lipids interacting with nucleic acids within formulated nucleic acid drugs. In some embodiments, formulated nucleic acid drugs are nucleic acid-based vaccines e.g., a coronavirus vaccine. Therefore, methods provided in the present disclosure are advantageous for bioanalytical analysis of target lipids that are interacting with nucleic acids.

In one aspect, provided herein is a composition for pretreating at least one target nucleic acid in a biological mixture prior to bioanalytical analysis, the composition including: a chaotropic agent selected from a substituted guanidine, a substituted amidine, a substituted quaternary amine, or a combination thereof. In some embodiments, the composition has a pH value of about 4 to about 10. In some embodiments, the composition further includes a protease, and/or a disulphide-reducing agent.

In some embodiments, the protease includes a serine protease, a threonine protease, a cysteine protease or a combination thereof. In some embodiments, the protease includes Proteinase K.

In some embodiments, the disulphide-reducing agent is selected from the group consisting of dithiothreitol (DTT), ethylenediaminetetraacetic acid (EDTA), 2-mercaptoethanol, 2-mercaptoethylamine-HCI, (Tris(2-Carboxyethyl) phosphine) (TCEP), N-ethylmaleimide, cystein, or glutathione.

In another aspect, provided herein is a composition for pretreating at least one target nucleic acid in a biological mixture prior to bioanalytical analysis, the composition including: a tert-butyl tetramethylguanidine, and Proteinase K, wherein the composition has a pH value of about 4 to about 10, wherein the sample comprises a biological mixture.

In one or more embodiments, substituted guanidine reagents according to the present disclosure include guanidines, wherein a hydrogen of one or more N—H group of the guanidines is substituted with an alkyl, aryl, cyclo, heteroatom containing, alkene, alkyne, PEG, PEO, etc. moiety. In some examples, the substitutions can be interconnected to form cyclic rings. As described herein, substituted guanidines are a group of compounds sharing the general structure $(R_1R_2N)(R_3R_4N)C{=}N{-}R$. In some embodiments, the substituted guanidine includes at least one from the group of tetramethylguanidine, tertbutyl tetramethylguanidine, triazabicyclodecene, or combinations thereof.

In one or more embodiments, substituted amidine reagents according to the present disclosure include amidines, wherein hydrogen of one or more N—H group of the amidines is substituted with an alkyl, aryl, cyclo, heteroatom containing, alkene, alkyne, PEG, PEO, etc. moiety.

In one embodiment, the substituted guanidine of tetramethylguanidine is 1,1,3,3-tetramethylguanidine with the chemical structure of

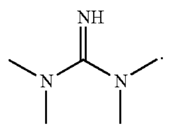

In another embodiment, the substituted guanidine of tertbutyl tetramethylguanidine is 2-tert-butyl-1,1,3,3-tetramethylguanidine with the chemical structure of

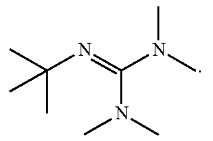

In another embodiment, the substituted guanidine of triazabicyclodecene is 1,5,7-triazabicyclo[4.4.0]dec-5-ene with the chemical structure of

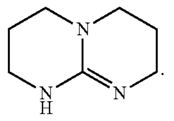

In any of the above embodiments, the substituted guanidine may be a guanidinium cation. In their conjugate acid form, guanidines are present as guanidinium cations, which are planar, symmetric ions bearing a highly stable 1+ charge. The resonance stabilization of the charge results in efficient solvation by water and high pKa values that are generally greater than 12. In neutral aqueous solutions, guanidines exists almost exclusively as guanidinium cations.

In some embodiments, the substituted quaternary amine is tetramethyl ammonium or tetraethylammonium, or combination thereof. In some embodiments, the substituted amidine comprises at least one from the group of hexanimidamide, acetamidine, propanimidamide, or combinations thereof.

In another aspect, provided herein is a method for detecting at least one target nucleic acid in a sample comprising a biological mixture, including the steps of: (a) incubating the sample with a composition including a chaotropic agent selected from a substituted guanidine, a substituted amidine, a substituted quaternary amine, or a combination thereof; and an optional protease, thereby disrupting one or more intermolecular interaction(s) of at least one target nucleic acid; (b) optionally heating the sample for a predetermined amount of time; (c) extracting the at least one target nucleic acid from the sample; and (d) detecting the at least one target nucleic acid using an analytical method.

In some embodiments, the analytical method comprises a mass spectroscopy. In some embodiments, the method further includes a step of quantifying the at least one target nucleic acid in the sample by using a mass spectrometry.

In some embodiments, the mass spectrometry is selected from the group consisting of Matrix-Assisted Laser Desorption/Ionization-Time-of-flight (MALDI-TOF), Electrospray-Ionization (ESI), Fourier Transform-Ion Cyclotron Resonance (FT-ICR), charge detection (CD), ion-mobility spectrometry (IMS), triple quadrupole, time of flight (TOF), and ion trap.

In any of the above embodiments, the length of at least one target nucleic acid is about 5 to about 100000 individual nucleotides. In some embodiments, the length of the target nucleic acid is about 5 to about 10000 individual nucleotides. In some embodiments, the length of the target nucleic acid is about 30 to about 2000 individual nucleotides. In certain embodiments, the length of the target nucleic acid is about 50 to about 1500 individual nucleotides. In certain embodiments, the length of the target nucleic acid is about 100 to about 1000 individual nucleotides.

In any of the above embodiments, the at least one target nucleic acid is selected from the group consisting of a single stranded DNA, a double stranded DNA, cDNA, a single stranded RNA, a double stranded RNA, a DNA/RNA hybrid, and a DNA/RNA mosaic nucleic acid. In some embodiments, the at least one target nucleic acid is selected from a DNA-based oligonucleotide or antisense oligonucleotide, a RNA-based oligonucleotide, siRNA, shRNA, tRNA, mRNA, snoRNA, stRNA, smRNA, pre- and pri-microRNA, other non-coding RNAs, ribosomal RNA, derivatives thereof, amplicons, and any combination thereof.

In some embodiments, the heating includes maintaining the temperature in a range from 50° C. to 100° C. In some embodiments, heating the sample includes heating the sample to a temperature ranging to at least 40° C. or from about 40° C. to about 100° C.

In some embodiments, the sample is or is derived from a biological fluid selected from the group consisting of blood, urine, spinal fluid, synovial fluid, sputum, semen, saliva, tears, gastric juices and extracts and/or dilutions/solutions thereof.

In another aspect, provided herein is a method of quantifying at least one target cationic lipid in a sample, wherein the sample includes at least one target cationic lipid interacting with a nucleic acid, the method including the steps of: (a) incubating the sample with a composition comprising a chaotropic agent selected from a substituted guanidine, a substituted amidine, a substituted quaternary amine, or a combination thereof; and an optional protease, thereby displacing the at least one target cationic lipid from the nucleic acid that is interacting with the at least one target cationic lipid; (b) optionally heating the sample for a predetermined amount of time; (c) extracting the at least one target cationic lipid from the sample; and (d) quantifying the at least one target nucleic acid using an analytical method.

In some embodiments, the method disrupts the microenvironment of the nucleic acid that is interacting with the at least one target cationic lipid, thereby displacing the at least one target cationic lipid from the nucleic acid.

In some embodiments, at least one target lipid e.g., a cationic lipid is selected from DLin-MC3-DMA, Heptadecan-9-yl 8-((2-hydroxyethyl) (6-oxo-6-(undecyloxy) hexyl) amino) octanoate, [(4-Hydroxybutyl)azanediyl]di(hexane-6,1-diyl) bis(2-hexyldecanoate), 1,2-di-O-octadecenyl-3-trimethylammonium propane (DOTMA), and 1,2-dioleoyl-3-trimethylammonium propane (DOTAP).

In some embodiments, the analytical method includes a chromatographic method coupled with a spectroscopic method. In some embodiments, the spectroscopic method is selected from the group consisting of ultraviolet spectroscopy, infrared spectroscopy, mass spectrometry, and nuclear magnetic resonance.

In some embodiments, the chromatographic method includes a reversed phase separation, a cation exchange separation, an anion exchange separation, an ion pair separation, normal phase separation, an ion mobility separation, a size-exclusion separation, a chiral separation, an affinity separation, a ligand exchange separation, a polar nonionic separation, or any combination thereof.

In some embodiments, the mass spectrometry method includes a mass spectroscopy selected from the group consisting of matrix-assisted laser desorption/ionization-time-of-flight (MALDI-TOF), electrospray-ionization (ESI), charge detection (CD), Fourier transform-ion cyclotron resonance (FT-ICR), ion-mobility spectrometry (IMS), triple quadrupole, time of flight (TOF), and ion trap.

In some embodiments, the mass spectrometry is triple quadrupole including a multiple reaction monitoring mode or a single reaction monitoring detection mode.

In some embodiments, the method further includes a step of buffer exchange, ion exchange and/or desalting prior to the step of incubating the sample.

In some embodiments, the method further includes a step of buffer exchange, ion exchange and/or desalting between the step of incubating the sample and the step of extracting the at least one target cationic lipid from the sample.

In some embodiments, the method further includes applying buffer exchange, ion exchange and/or desalting processes to the extracted at least one target cationic lipid prior to the step of quantifying the at least one target nucleic acid.

In any of the above embodiments, concentration of the chaotropic agent is between about 0.01 mM and about 10 M, between about 0.1 mM to about 1 M, between about 0.1 mM to about 100 mM or between about 0.1 mM to 10 mM.

The concentration of the chaotropic agent agents, when described herein, is referring to the buffered solution. The buffered solution can include common buffers and ionic strength adjusting salts. Common buffers include phosphate, tris(hydroxymethyl)aminomethane, tris bis propane, triethyl amine, and other common buffers. Common ionic strength adjusting salts include NaCl, KCl, $Ca^{2+}$, or other divalent or monovalent cations and anions.

The methods and compositions disclosed herein advantageously provide ways to efficiently extract oligonucleotides or other metabolites such as lipids that are interacting with the oligonucleotides from complex biological matrices. Efficient extraction of oligonucleotides from complex matrices paves the way for accurate and robust detection and quantification methodologies.

The methods and compositions provided in this disclosure are also advantageous for rapidly and effectively disrupting the intermolecular interactions that can interfere with the bioanalytical analysis of a target nucleic acid.

The methods and compositions provided in this disclosure also eliminate the need of using existing lysis solutions containing high concentrations of denaturants removal of which is challenging prior to an analytical method.

In addition, in some embodiments, the composition used in the present methods e.g. chaotropic agent selected from a substituted guanidine, a substituted amidine, a substituted quaternary amine, or a combination thereof, an optional protease, and/or an optional disulfide-reducing agent is compatible with most of the downstream analytical methods e.g., an LC-MS method.

BRIEF DESCRIPTION OF THE DRAWINGS

The technology will be more fully understood from the following detailed description taken in conjunction with the accompanying drawings, in which.

DETAILED DESCRIPTION

Figure 1:
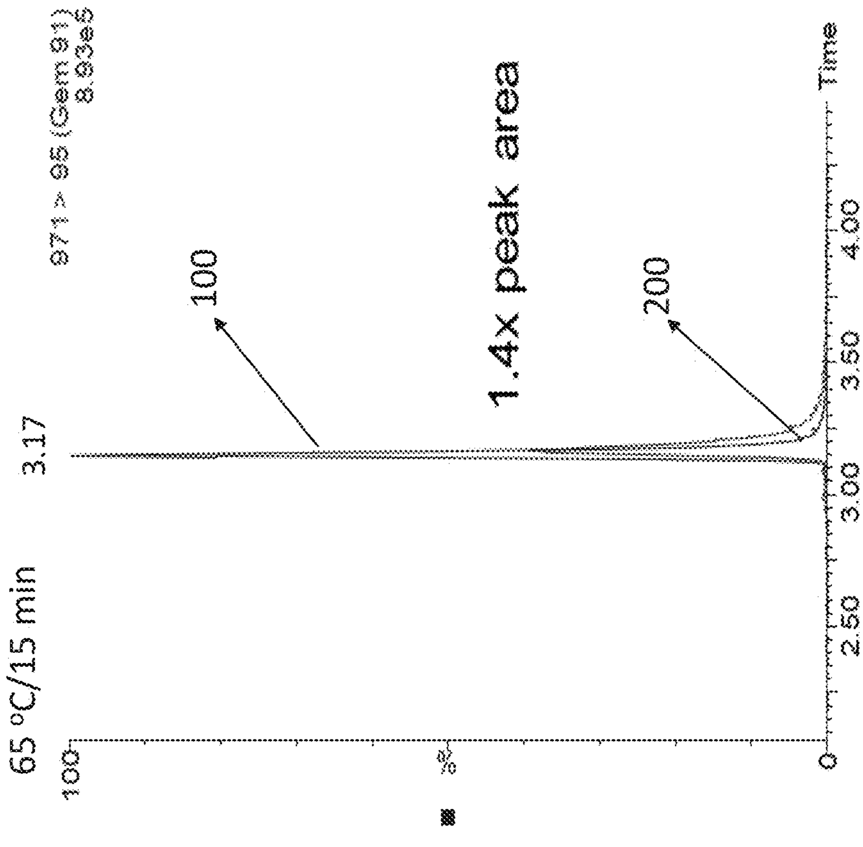
FIG. 1 shows chromatographic peak area comparison of GEM 91 (pretreated at 65° C. for 15 min) both with (100) and without (200) 50 mM tert-butyl-tetramethylguanidine. The results demonstrate the impact of using tert-butyl-tetramethylguanidine for pretreatment of GEM91 on extraction recovery efficiencies. In this example, GEM 91 a fully thioated 25mer, was prepared in rat plasma and incubating at 65 C for 15 minutes. Calculated recovery yields of GEM 91 were shown to be greater than 95% with the 50 mM tert-butyl-tetramethylguanidine (100) and only 62% without the 50 mM tert-butyl-tetramethylguanidine (200).

A huge challenge facing scientists developing oligonucleotide therapeutics is the difficult extraction protocols and analytical methods needed to identify metabolites. The most commonly used techniques to facilitate extraction include liquid-liquid extraction and solid phase extraction, either used individually or as a combination of both. However, these traditional techniques suffer from low extraction recoveries and prolonged preparation times.

A similar analytical challenge is being encountered with the analysis of formulated nucleic acid drug products. Lipid nanoparticles are an important facet of the approved siRNA nucleic acid therapies and for the emergency authorized mRNA vaccines (e.g., vaccines for preventing the spread of COVID-19). In these final drug products, lipids are used to encapsulate the nucleic acid and thereby provide a means for them to be endocytosed into cells. Very often a cationic lipid is included in the composition of the lipid nanoparticle, and the role of this molecule is to directly interact with the phosphodiester backbone of the nucleic acid. With enough ion paired cationic lipid, a so-called inverse micelle is formed through which lipid encapsulation can be completed with the addition of cholesterol, a phosphotidyl choline lipid, and/or a pegylated lipid. As the lipid nanoparticle is designed with a strong cationic lipid to nucleic acid interaction causes analytical challenges. For instance, LC and MS analysis on LNP encapsulated nucleic acids can result in an undesirably heterogenous mixture of metastable species. LNP nucleic acid can be directly subjected to reversed phase or hydrophilic interaction liquid chromatography, but without special care and sample pretreatment, it is common to chromatograph only a small percentage of the nucleic acid as a fully dissociated and it is more likely to find a metastable complex of the nucleic associated with one or more lipids from the LNP. Sometimes this is seen in a unique population of peaks within the chromatogram, or it can be seen in the mass spectrometry data as adducted ions.

Chaotropic agents of the present disclosure are shown to be powerful effectors of protein structure. As denaturants, it has been found that these compounds can disrupt common protein structures at sub-millimolar concentrations. In the present technology, this denaturation power is used advantageously to isolate and/or extract one or more nucleic acids from complex matrices prior to bioanalytical methods.

While not wishing to be bound by theory, it is reasonable to suggest that these reagents are unique in being able to strongly ion pair to anionic nucleic acids residues while simultaneously affecting the local microenvironment around the site of ion pairing. In turn, it could be possible that these reagents disrupt the solvated environment so as to be disruptive to protein domains and molecules that would otherwise have a propensity to interact with the nucleic acid.

The present compositions and methods are also useful for extracting other metabolites such as lipids e.g., a cationic lipid that are interacting with nucleic acids within a complex matrix. In the case of a cationic lipid interacting with a nucleic acid molecule, the chaotropic agents of the present disclosure can also have properties that facilitate the displacement of the cationic lipid. The substituted guanidine, amidine or quaternary amine reagents of the present disclosure can ion pair with a phosphodiester or phosphorothioate site to exchange away the cationic lipid and also bring hydrophobic substituents to help displace any molecules from having Van der Waals, pi-pi or hydrophobic interactions with the nucleobases or conjugated residues of the nucleic acid. Protein denaturation effects from these reagents might be equally significant to the instant disclosure. Because of the noted ion pairing effects, these substituted guanidino, amidino, and quaternary amine reagents might be particularly advantageous for simultaneously denaturing protein structures, particularly when heat is applied to the sample.

As used herein, the term "about" means that the numerical value is approximate and small variations would not significantly affect the practice of the disclosed embodiments. Where a numerical limitation is used, unless indicated otherwise by the context, "about" means the numerical value can vary by ±10% and remain within the scope of the disclosed embodiments.

As used herein, the term "sample" refers to any medium that includes an analyte (e.g. a target nucleic acid or a target lipid molecule) to be processed using the compositions and methods according to the present disclosure. A sample may be selected from an agricultural sample, an environmental sample, or a biological sample. A biological sample may include, but is not limited to, for example, a formulated nucleic acid base drug, a formulated nucleic acid base vaccine, a clinical specimen (e.g., blood, plasma, serum, sputum, tissue, urine, saliva, sample/fluid from the respiratory tract, etc.), and cosmetic and pharmaceutical products (e.g., lotions, creams, ointments, solutions, medicines, eye and ear drops, etc.).

As used herein, the term "pretreating" refers to any steps or methods that treat a sample for downstream analysis of a target nucleic acid. Sample preparation may comprise various procedures needed to process the raw sample so that it is amenable to further analytical method, e.g. LC-MS method. It is important to note that at least one single sample preparation step should be compatible with downstream detection method in order to obtain optimal results.

The oligonucleotides or the lipids of the present disclosure be purified before or after pretreating step if necessary to remove substances which could be harmful (e.g. toxins), dangerous (e.g. infectious) or might interfere with the downstream analysis or the sensitivity of that analysis (e.g. metals, salts, protein, lipids). Purification may involve techniques such as chemical extraction with salts, chloroform or phenol, sedimentation centrifugation, chromatography or other techniques known to those of ordinary skill in the art.

As used herein, the term "oligonucleotide" or "oligo" or "oligomer" is intended to encompass not only a single "oligonucleotide" but also a plurality of "oligonucleotides". Refers to any polymer consisting of two or more nucleotides, nucleosides, nucleobases or related compounds. The oligonucleotide can be DNA and/or RNA and/or an analogue thereof. Oligonucleotides are polymers or oligomers of nitrogenous bases in which the nitrogenous bases are connected by means of sugar phosphate bonds (sugar-phosphate structure).

As used herein, the term "target nucleic acid" refers to a nucleic acid comprising a "target sequence" to be analyzed. Target nucleic acids may be DNA or RNA and may be either single-stranded or double-stranded. The target nucleic acid may include other sequences besides the target sequence that may not be analyzed.

In certain embodiments the size of the target nucleic acid may 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65,66, 67, 68, 69, 70, 71, 72, 73,74, 75, 76, 77, 78, 79, 80, 81, 82, 83, 84, 85, 86, 87, 88, 89,90,91, 92,93, 94, 95, 96, 97,98, 99, 100, 110, 120, 130, 140, 150, 160, 170, 180, 190, 200, 210, 220, 230, 240, 250, 275,300, 325, 350, 375,400, 425,450, 475, 500, 525,550, 575,600, 625, 650, 675, 700, 725,750, 775, 800, 825, 850, 875,900, 925,950, 975, 1000, 1100, 1200, 1300, 1400, 1500, 1750, 2000, 2250, 2500 or greater contiguous nucleotides, and any range derivable therein.

As used herein, the term "disulfide bond reducing agent" refers to an agent that reduces disulfide bonds, e.g., in proteins, in nucleic acids. Non-limiting examples include, dithiothreitol (DTT), ethylenediaminetetraacetic acid (EDTA), 2-mercaptoethanol, 2-mercaptoethylamine-HCl, (Tris(2-Carboxyethyl)phosphine) (TCEP), N-ethylmaleimide, cystein, or glutathione.

As used herein, the term "chaotrope" can include, e.g., a chemical that can disrupt the structure of water and/or promote the solubility of nonpolar substances in polar solvents such as water. Such behavior by chaotropes often results in the unfolding and inactivation of proteins or nucleic acids.

The composition used in the present disclosure can cause denaturation of a target nuclease.

EXAMPLES

The following examples are included to demonstrate preferred embodiments of the technology. However, those of skill in the art should, in light of the present disclosure, appreciate that many changes can be made in the specific embodiments which are disclosed and still obtain a like or similar result without departing from the spirit and scope of the technology.

Example 1: Extraction of an Anti-Sense Oligonucleotide from a Biological Sample to Compare Multiple Reaction Monitoring (MRM) Peak Areas for Samples that are Pretreated with or without Tert-Butyl-Tetramethylguanidine The plasma samples for solid phase extraction (SPE) were prepared by taking 200 μL aliquots of plasma and spiking in Gem 132 at a concentration of 16 μg/mL and Gem 91 at a concentration of 5 μg/mL for each sample. To each sample, 40 μL of lysis buffer consisting of 60 mM Tris (pH 8.5), or a lysis buffer consisting of 60 mM Tris (pH 8.5), and 50 mM 2-tert-butyl-1,1,3,3-tetramethylguanidine was added. 40 μL of 20 mM dithiothreitol and 20 μL of 100 mg/mL proteinase K were also added. Samples were vortexed for around 20 seconds and mixed at 65° C. for 15 min at 400 RPM.

The SPE protocol was performed using a positive pressure manifold (Otto SPEcialist positive pressure manifold, available from Waters Technologies Corporation, Milford, MA) and the SPE protocol outlined below. The sample is quenched with 600 µL 50 mM ammonium acetate, pH 5.5 before loading.

Analyses of these samples were performed using a LC system (Waters ACQUITY UPLC I-Class LC system) and the separation method outlined below. FIG. 1 presents the peak areas of Gem91 (transition from 971→95 m/z) after SPE was performed with (100) and without (200) 50 mM 2-tert-butyl-1,1,3,3-tetramethylguanidine in the lysis buffer. Calculated recovery yields of GEM 91 were shown to be greater than 95% with the 50 mM tert-butyl-tetramethylguanidine (100) and only 62% without the 50 mM tert-butyl-tetramethylguanidine (200). The results demonstrate that how using tert-butyl-tetramethylguanidine for pretreatment of GEM91 leads to increase on extraction recovery efficiencies.

TABLE 1

| SPE Protocol for Example 1 | |
|---|---|
| **Test Conditions** | |
| SPE Plate | Hybridized Silica C18, 300 angstroms, bonded with an amino ligand, 4 mg/well |
| Sample for Digestion | 200 µL rat plasma (Gem 91 @ 5 ug/mL/Gem 132 @ 16 ug/mL) |
| **Protocol** | |
| Conditioning | 2 × 200 µL methanol |
| Equilibration | 1 × 200 µL 50 mM ammonium acetate, pH 5.5 |
| Load | Load quenched sample volume |
| Wash 1 | 2 × 200 µL 50 mM ammonium acetate, pH 5.5 |
| Wash 2 | 1 × 200 µL 20% methanol |
| Elute 1 | 2 × 50 µL 50 mM triethylamine in 30% methanol |
| Elute 2 | 2 × 50 µL 1% etidronic acid, pH 9 in 30% methanol |
| Reconstitute | 100 µL of 1% 1,1,1,3,3,3-hexafluoro-2-propanol, 0.1% N,N-diisopropylethylamine in water |

TABLE 2

| Separation details for Example 1 | |
|---|---|
| **Test Conditions** | |
| Column | Hybrid Silica C18, 130 angstroms, 1.7 µm packed within a C2 coated stainless steel column 2.1 × 50 mm (with C2 coated titanium frit) |
| Sample | Collected eluants from SPE protocol |
| **Solvent Conditions** | |
| Solvent Line A | 1% 1,1,1,3,3,3-hexafluoro-2-propanol, 0.1% N,N-diisopropylethylamine in water |
| Solvent Line B | 0.75% 1,1,1,3,3,3-hexafluoro-2-propanol, 0.375% N,N-diisopropylethylamine in 65:35 acetonitrile:water |
| Column Temperature | 60° C. |
| Injection Volume | 10 µL |
| UV Detection | 260 nm |
| **MS Conditions** | |
| Mode | ESI negative |
| Acquisition | MRM |
| Capillary | 2.0 kV |
| Source Temperature | 100° C. |
| Cone Gas Flow | 150 L/Hr |
| Collision Gas Flow | 0.2 mL/min |
| Nebulizer Gas Flow | 7 Bar |

TABLE 2-continued

| Separation details for Example 1 | |
|---|---|
| Desolvation Temperature | 500° C. |
| Desolvation Gas | 1000 L/h |
| MRM Transition | 971 -> 95 m/z |

Gradient Table:

| Time (min) | Flow Rate (mL/min) | % A | % B | Curve |
|---|---|---|---|---|
| Initial | 0.600 | 90.0 | 10.0 | Initial |
| 1.00 | 0.600 | 90.0 | 10.0 | 6 |
| 1.50 | 0.600 | 50.0 | 50.0 | 6 |
| 3.00 | 0.600 | 45.0 | 55.0 | 6 |
| 3.50 | 0.600 | 40.0 | 60.0 | 6 |
| 4.00 | 0.600 | 30.0 | 70.0 | 6 |
| 4.10 | 0.600 | 5.0 | 95.0 | 6 |
| 4.50 | 0.600 | 5.0 | 95.0 | 6 |
| 4.60 | 0.600 | 90.0 | 10.0 | 6 |
| 5.00 | 0.600 | 90.0 | 10.0 | 6 |

Example 2: MRM Peak Area of GEM 91 at Different Concentrations of Proteinase K The plasma samples for SPE were prepared by taking 200 µL aliquots of plasma and spiking in Gem 132 at a concentration of 16 µg/mL and Gem 91 at a concentration of 5 ug/mL for each sample. To each sample, 40 µL of lysis buffer consisting of 60 mM Tris (pH 8.5), and 50 mM 2-tert-butyl-1,1,3,3-tetramethylguanidine was added. 40 µL of 20 mM dithiothreitol and 20 µL of either 10, 50, or 100 mg/mL proteinase K were also added. Samples were vortexed for around 20 seconds and mixed at 65° C. for 15 min at 400 RPM.

The SPE protocol was performed using the Otto SPEcialist (positive pressure manifold, available from Waters Technologies Corporation, Milford, MA) and the SPE protocol outlined below.

Figure 2:
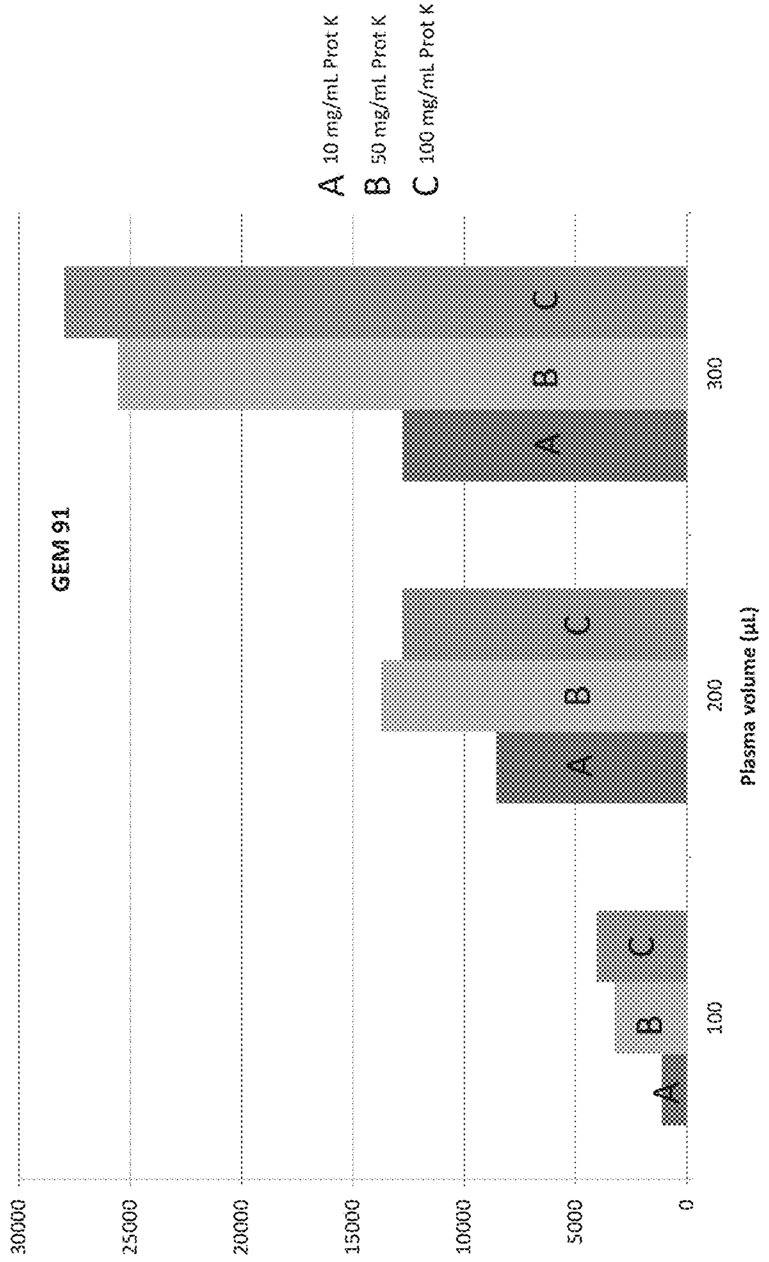
FIG. 2 displays analyte peak area of GEM 91 (pretreated at 65° C. for 15 min) at different concentrations of Proteinase K.

Analyses of these samples were performed using a Waters ACQUITY UPLC I-Class LC system and the separation method outlined below. FIG. 2 presents the peak areas of Gem91 (transition from 971→95 m/z) after SPE was performed with the varying proteinase K concentrations. FIG. 2 shows that regardless of plasma volume that is pretreated, the recovery efficiencies of Gem 91 increases as the concentration of proteinase K increases from 10 mg/ml to 100 mg/ml. Without wishing to be bound by theory, it seems that proteinase K can strength the effect of 2-tert-butyl-1,1,3,3-tetramethylguanidine to isolate/extract Gem 91 from the rat plasma. Proteinase K may result in proteolysis of certain proteins or metabolites that are interacting with Gem 91 which can explain the increase in recovery efficiencies of Gem 91 as concentration of proteinase K is increased.

TABLE 3

| SPE Protocol for Example 2 | |
|---|---|
| **Test Conditions** | |
| SPE Plate | Hybridized Silica C18, 300 angstroms, bonded with an amino ligand, 4 mg/well |
| Sample for Digestion | 200 µL rat plasma (Gem 91 @ 5 µg/mL/Gem 132 @ 16 µg/mL) or 200 µL rat plasma (Gem 132 @ 16 µg/mL) |

TABLE 3-continued

| SPE Protocol for Example 2 | |
|---|---|
| Protocol | |
| Conditioning | 1 × 200 µL methanol |
| Equilibration | 1 × 200 µL 50 mM ammonium acetate, pH 5.5 |
| Load | Load sample volume |
| Wash 1 | 1 × 200 µL 50 mM ammonium acetate, pH 5.5 |
| Wash 2 | 1 × 200 µL 30% methanol |
| Elute 1 | 2 × 50 µL 50 mM triethylamine in 50% methanol |
| Elute 2 | 2 × 50 µL 1% etidronic acid, pH 9 in 50% methanol |
| Reconstitute | 100 µL of 1% 1,1,1,3,3,3-hexafluoro-2-propanol, 0.1% N,N-diisopropylethylamine in water |

TABLE 4

| Separation details for Example 2 | |
|---|---|
| Test Conditions | |
| Column | Hybrid Silica C18, 130 angstroms, 1.7 µm packed within a C2 coated stainless steel column 2.1 × 50 mm (with C2 coated titanium frit) |
| Sample | Collected eluents from SPE protocol |
| Solvent Conditions | |
| Solvent Line A | 1% 1,1,1,3,3,3-hexafluoro-2-propanol, 0.1% N,N-diisopropylethylamine in water |
| Solvent Line B | 0.75% 1,1,1,3,3,3-hexafluoro-2-propanol, 0.375% N,N-diisopropylethylamine in 65:35 acetonitrile:water |
| Column Temperature | 60° C. |
| Injection Volume | 10 µL |
| UV Detection | 260 nm |
| MS Conditions | |
| Mode | ESI negative |
| Acquisition | MRM |
| Capillary | 2.0 kV |
| Source Temperature | 100° C. |
| Cone Gas Flow | 150 L/Hr |
| Collision Gas Flow | 0.2 mL/min |
| Nebulizer Gas Flow | 7 Bar |
| Desolvation Temperature | 500° C. |
| Desolvation Gas | 1000 L/h |
| MRM Transition | 971 -> 95 m/z |

Gradient Table:

| Time (min) | Flow Rate (mL/min) | % A | % B | Curve |
|---|---|---|---|---|
| Initial | 0.600 | 90.0 | 10.0 | Initial |
| 1.00 | 0.600 | 90.0 | 10.0 | 6 |
| 1.50 | 0.600 | 50.0 | 50.0 | 6 |
| 3.00 | 0.600 | 45.0 | 55.0 | 6 |
| 3.50 | 0.600 | 40.0 | 60.0 | 6 |
| 4.00 | 0.600 | 30.0 | 70.0 | 6 |
| 4.10 | 0.600 | 5.0 | 95.0 | 6 |
| 4.50 | 0.600 | 5.0 | 95.0 | 6 |
| 4.60 | 0.600 | 90.0 | 10.0 | 6 |
| 5.00 | 0.600 | 90.0 | 10.0 | 6 |

Example 3: Displacement of Cationic Lipids from an LNP Encapsulated mRNA Sample With this example, RNA molecules contained within lipid nanoparticles are submitted for analytical testing, such as an RNA integrity test wherein it is of interest to check a drug product for hydrolytic damage and fragmentation. It might also be of interest to apply this sample treatment protocol to displace the cationic lipid from the mRNA to thereby allow quantitation and stoichiometric measurements of the lipid nanoparticle composition. Example cationic lipids that are used in lipid nanoparticle formulated drug products include but are not limited to DLin-MC3-DMA, Heptadecan-9-yl8-((2-hydroxyethyl) (6-oxo-6-(undecyloxy) hexyl) amino) octanoate, [(4-Hydroxybutyl)azanediyl]di(hexane-6,1-diyl) bis(2-hexyldecanoate), 1,2-di-O-octadecenyl-3-trimethylammonium propane (DOTMA), and 1,2-dioleoyl-3-trimethylammonium propane (DOTAP).

Figure 3:
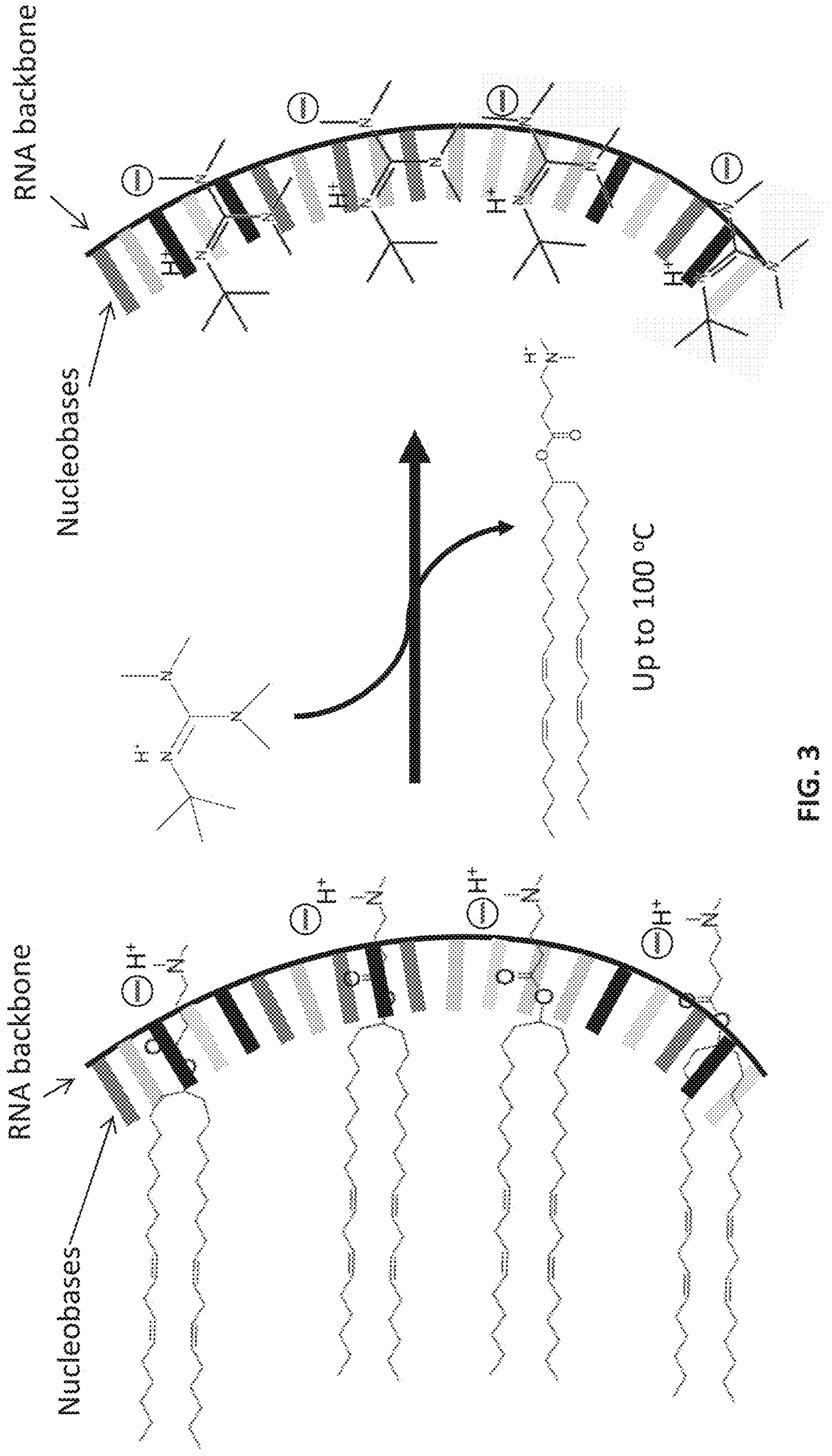
FIG. 3 displays schematic representation of the displacement of cationic lipids from a nucleic acid.

A schematic for this protocol is provided in FIG. 3. The lipid nanoparticle (LNP) encapsulated RNA is treated with a 1 mM to 1 M concentration of substituted guanidino, amidino or quaternary amino reagent. An EPO mRNA encapsulated in a lipid nanoparticle comprised of DLin-MC3-DMA (CAS #1224606-06-7), DSPC (CAS #816-94-4), cholesterol (CAS #57-88-5) and PEG2000-C-DMG (CAS 1397695-86-1) is treated with 50 mM 2-tert-butyl-1,1,3,3-tetramethylguanidine and optionally heated for 5 minutes at 90° C. In addition, LNP encapsulated patisirin is treated with 1 M 2-tert-butyl-1,1,3,3-tetramethylguanidine at room temperature. Subsequently, these samples are analyzed by reversed phase, mixed mode ion exchange reversed phase, or hydrophilic interaction liquid chromatography coupled with either UV, fluorescence, evaporative light scattering, charged aerosol, refractive index, dynamic light scattering and/or mass spectrometric detection. In this example, a substituted guanidino, amidino or quaternary amino reagent that will have little to no retention on the chromatographic column is preferred. In some embodiments, buffer exchange, ion exchange and/or desalting might be performed in combination with this displacement of the cationic lipid.

While this disclosure has been particularly shown and described with reference to example embodiments thereof, it will be understood by those skilled in the art that various changes in form and details may be made therein without departing from the scope of the technology encompassed by the appended claims. For example, other chromatography systems or detection systems can be used.

What is claimed is:

1. A composition for pretreating at least one target nucleic acid in a biological mixture prior to bioanalytical analysis, the composition comprising: a chaotropic agent, a protease, and a disulfide-reducing agent, wherein the chaotropic agent is selected from a substituted guanidine, a substituted amidine, a substituted quaternary amine, or a combination thereof, wherein the composition has a pH value of about 4 to about 10.

2. The composition of claim 1, wherein the chaotropic agent comprises tert-butyl tetramethylguanidine, and the protease comprises Proteinase K.

3. The composition of claim 1, wherein the substituted guanidine comprises at least one from the group of tetramethylguanidine, tertbutyl tetramethylguanidine, triazabicyclodecene, or combinations thereof.

4. The composition of claim 3, wherein the substituted guanidine of tetramethylguanidine is 1,1,3,3-tetramethylguanidine with the chemical structure of

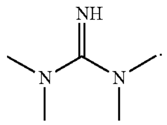

5. The composition of claim 3, wherein the substituted guanidine of tertbutyl tetramethylguanidine is 2-tert-butyl-1,1,3,3-tetramethylguanidine with the chemical structure of

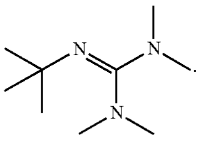

6. The composition of claim 3, wherein the substituted guanidine of triazabicyclodecene is 1,5,7-triazabicyclo [4.4.0]dec-5-ene with the chemical structure of

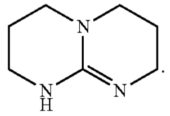

7. The composition of claim 1, wherein the substituted guanidine is a guanidinium cation.

8. The composition of claim 1, wherein the substituted quaternary amine is tetramethyl ammonium or tetraethyl-ammonium, or combination thereof.

9. The composition of claim 1, wherein the substituted amidine comprises at least one from the group of hexanimidamide, acetamidine, propanimidamide, or combinations thereof.

10. The composition of claim 1, wherein the protease comprises a serine protease, a threonine protease, a cysteine protease or a combination thereof.

11. A method for detecting at least one target nucleic acid in a sample comprising a biological mixture, comprising the steps of:

a) incubating the sample with a composition comprising a chaotropic agent selected from a substituted guanidine, a substituted amidine, a substituted quaternary amine, or a combination thereof; and a protease, thereby disrupting one or more intermolecular interaction(s) of at least one target nucleic acid;

b) optionally heating the sample for a predetermined amount of time;

c) extracting the at least one target nucleic acid from the sample; and d) detecting the at least one target nucleic acid using an analytical method.

12. The method of claim 11, wherein the analytical method comprises a mass spectroscopy.

13. The method of claim 11, further comprising a step of quantifying the at least one target nucleic acid in the sample by using a mass spectrometry.

14. The method of claim 11, wherein the length of at least one target nucleic acid is about 5 to about 10000 individual nucleotides.

15. The method of claim 11, wherein the at least one target nucleic acid is selected from a DNA-based oligonucleotide or antisense oligonucleotide, a RNA-based oligonucleotide, siRNA, shRNA, RNA, mRNA, snoRNA, stRNA, smRNA, pre- and pri-microRNA, other non-coding RNAs, ribosomal RNA, derivatives thereof, amplicons, and any combination thereof.

16. The method of claim 11, wherein the heating comprises maintaining the temperature in a range from 50° C. to 100° C.

17. The method of claim 11, wherein the sample is or is derived from a biological fluid selected from the group consisting of blood, urine, spinal fluid, synovial fluid, sputum, semen, saliva, tears, gastric juices and extracts and/or dilutions/solutions thereof.

18. A method of quantifying at least one target cationic lipid in a sample, wherein the sample comprises at least one target cationic lipid interacting with a nucleic acid, the method comprising the steps of:

a) incubating the sample with a composition comprising a chaotropic agent selected from a substituted guanidine, a substituted amidine, a substituted quaternary amine, or a combination thereof; and an optional protease, thereby displacing the at least one target cationic lipid from the nucleic acid that is interacting with the at least one target cationic lipid;

b) optionally heating the sample for a predetermined amount of time;

c) extracting the at least one target cationic lipid from the sample; and d) quantifying the at least one target cationic lipid using an analytical method.

* * * * *